US011174287B2

(12) United States Patent
Moudgil et al.

(10) Patent No.: US 11,174,287 B2
(45) Date of Patent: Nov. 16, 2021

(54) CENTRAL NERVOUS SYSTEM HOMING PEPTIDES AND USES THEREOF

(71) Applicants: Kamal Moudgil, Silver Spring, MD (US); Bodhraj Acharya, Baltimore, MD (US)

(72) Inventors: Kamal Moudgil, Silver Spring, MD (US); Bodhraj Acharya, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 16/477,125

(22) PCT Filed: Jan. 10, 2018

(86) PCT No.: PCT/US2018/013159
§ 371 (c)(1),
(2) Date: Jul. 10, 2019

(87) PCT Pub. No.: WO2018/132467
PCT Pub. Date: Jul. 19, 2018

(65) Prior Publication Data
US 2019/0359651 A1 Nov. 28, 2019

Related U.S. Application Data

(60) Provisional application No. 62/444,776, filed on Jan. 10, 2017.

(51) Int. Cl.
| | |
|---|---|
| *C07K 7/06* | (2006.01) |
| *A61K 47/69* | (2017.01) |
| *A61K 47/64* | (2017.01) |
| *A61P 25/00* | (2006.01) |
| *A61P 29/00* | (2006.01) |
| *A61K 49/14* | (2006.01) |
| *G01N 33/68* | (2006.01) |
| *A61K 38/00* | (2006.01) |

(52) U.S. Cl.
CPC ............... *C07K 7/06* (2013.01); *A61K 47/64* (2017.08); *A61K 47/6911* (2017.08); *A61K 47/6927* (2017.08); *A61K 47/6929* (2017.08); *A61K 49/14* (2013.01); *A61P 25/00* (2018.01); *A61P 29/00* (2018.01); *G01N 33/6896* (2013.01); *A61K 38/00* (2013.01)

(58) Field of Classification Search
CPC .................. C07K 7/06; A61K 47/6911
See application file for complete search history.

(56) References Cited

U.S. PATENT DOCUMENTS

| | | | | |
|---|---|---|---|---|
| 7,355,026 | B2 * | 4/2008 | Alexandrov | C07H 21/04 536/23.6 |
| 7,399,903 | B2 * | 7/2008 | Wang | C12N 15/8273 435/320.1 |
| 7,569,389 | B2 * | 8/2009 | Feldmann | C07K 14/415 435/419 |
| 7,745,391 | B2 * | 6/2010 | Mintz | A61P 31/00 514/19.3 |
| 9,012,723 | B2 * | 4/2015 | Guo | C12N 15/8261 800/285 |
| 2004/0029129 | A1 * | 2/2004 | Wang | C07K 14/30 435/6.18 |
| 2004/0034888 | A1 * | 2/2004 | Liu | C07H 21/04 800/289 |
| 2004/0123343 | A1 * | 6/2004 | La Rosa | C07K 14/415 800/278 |
| 2006/0134103 | A1 * | 6/2006 | Hawley | C12N 9/1088 424/133.1 |
| 2011/0130342 | A1 | 6/2011 | Laakkonen | |
| 2017/0039314 | A1 * | 2/2017 | Bremel | A61K 39/04 |

OTHER PUBLICATIONS

Amselem et al., 2011, Genomic Analysis of the Necrotic Fungal Pathogens Sclerotinia sclerotiorum and Botrytis cinerea, PLoS Genetics, 7(8): e1002230 (27 pages).*
The Bactrian Camels Genome Sequencing and Analysis Consortium, 2011, Genome sequences of wild and domestic Bactrian camels, Nature Communications, 3: 1202 (8 pages).*
Xu et al., 2007, Evolution of Symbiotic Bacteria in the Distal Human Intestine, PLoS Biology, 5(7): e156-1574-1586.*
UniproKB—C8S2Q9, Nov. 3, 2009. htt//www.uniprot.org/uniport/C8S209> amino acids 317-379.
International Search Report form Appl. No. PCT/US2018/013159, dated May 15, 2018.

* cited by examiner

*Primary Examiner* — Amber D Steele
(74) *Attorney, Agent, or Firm* — Nevrivy Patent Law Group P.L.L.C.

(57) ABSTRACT

The present invention provides homing peptides that localize in central nervous system tissue characterized by neuroinflammation and methods of using the same.

21 Claims, 15 Drawing Sheets
Specification includes a Sequence Listing.

Fig. 1

MOG/CFA s.c.
+
pertussis toxin i.p.

MOG = 200 µg / mice
Toxin= 400 ng/mice 0 hr and 48 hr

\* animal may need soft food
\*\* diet gel and hydrogel must be given

| Score | Sign | Description |
|---|---|---|
| 0.5 | Limp tail | |
| 1.0 | Complete tail flaccid | The tail completely limps and drops |
| 2 | Delay in righting reflex, hind limb weakness | animal has difficulties to return to his feet when it is laid back, walking is slightly wobbly. |
| 3 | Flaccid paralysis in 1 hind limb | walking is wobbly, legs are unsteady \* |
| 4 | Flaccid paralysis in both hind limb | animal drags the hind limbs because they are paralyzed, sometimes animal cannot move \*\* |
| 5 | Moribund | |

Fig. 5

| Peptide sequence | Clone frequency | Frequency (percent) | Example of homologous proteins | Homologous motif | Accession number |
|---|---|---|---|---|---|
| KRSS SEQ ID NO:1 | 2/44 (4.5%) | 4/4 (100%) 4/4 (100%) 4/4 (100%) | • glucose-6-phosphate dehydrogenase (h) <br>• T cell receptor alpha (m) <br>• interleukin 17A | [20]KRSS[23] SEQ ID NO:1 <br>[41]KRSS[44] SEQ ID NO:1 <br>[15]KRSS[18] SEQ ID NO:1 | AAA52503.1 <br>AAB31931.1 <br>ADJ56412.1 |
| RAKGRDA SEQ ID NO:9 | 3/44 (6.9%) | 6/7 (86%) | zinc finger protein (m) | [2036]RAKGRD[2041] SEQ ID NO:24 | XP006544428.1 |

Fig. 6

| Matched Sequence | Elm Description | Cell Compartment | Probability |
|---|---|---|---|
| KRS | N-terminal motif that initiates protein degradation by binding to the UBR-box of N-recognins. This N-degron variant comprises N-terminal Arg or Lys as destabilizing residue. | cytosol | 2.064e-04 |
| KRS | NEC1/NEC2 cleavage site (K-R-\|-X). | extracellular, Golgi apparatus, Golgi membrane | 3.903e-03 |
| RAK | N-terminal motif that initiates protein degradation by binding to the UBR-box of N-recognins. This N-degron variant comprises N-terminal Arg or Lys as destabilizing residue. | cytosol | 2.064e-04 |

Testing in EAE Mice

Fig. 13
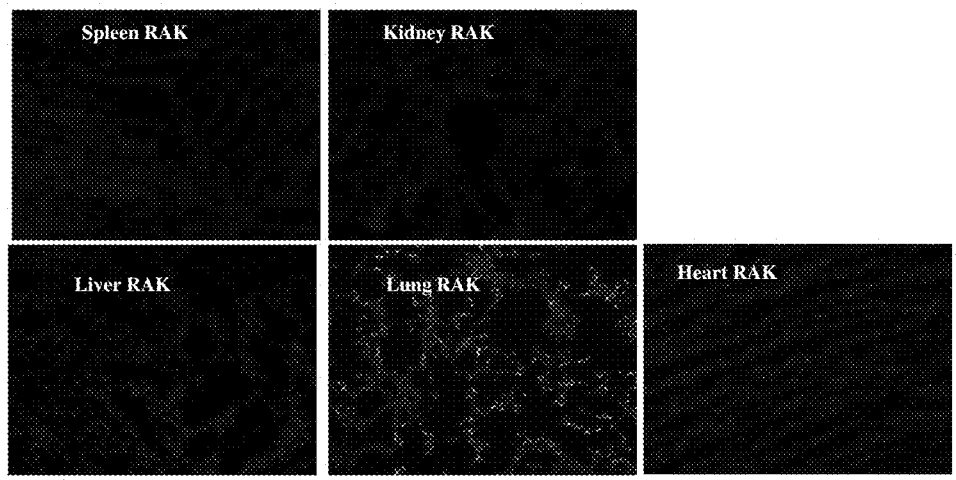

CENTRAL NERVOUS SYSTEM HOMING PEPTIDES AND USES THEREOF

CROSS-REFERENCE TO RELATED APPLICATIONS

This application is the U.S. National Stage application under 35 U.S.C. § 371 of International Appl. No.: PCT/US2018/013159, filed Jan. 10, 2018, which claims the benefit of U.S. Provisional Appl. No. 62/444,776 filed on Jan. 10, 2017, the contents of which are hereby incorporated by reference in their entirety.

STATEMENT OF FEDERALLY SPONSORED RESEARCH AND DEVELOPMENT

This invention was made with government support under Grant Number NS082918 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable sequence listing submitted concurrently herewith and identified as follows: One 4,248 Byte ASCII (Text) file named "sequence_listing_ST25.txt," created on May 12, 2021.

FIELD OF THE INVENTION

The field of the invention relates to homing peptides that can be used in the diagnosis and detection of disease as well as for enhanced targeting of therapeutic agents to the central nervous system.

BACKGROUND OF THE INVENTION

The following description of the background of the invention is provided to aid in understanding the invention, but is not admitted to be or to describe prior art to the invention.

Multiple sclerosis (MS) is a chronic debilitating autoimmune disease involving inflammation and damage to the central nervous system (CNS) (brain and spinal cord). The T cells reactive against myelin and other CNS antigens cross the blood-brain barrier and cause inflammation and tissue damage. Two of the main challenges for researchers working in the field of MS are 1) to define the underlying mechanisms that render the CNS highly prone to an autoimmune attack, and 2) to devise novel ways to direct the orally-administered or injected drugs primarily into the CNS to enhance their efficacy while minimizing adverse effects.

The targeted delivery of drugs, prodrugs, or other therapeutic agents to the cells where they are needed can potentially improve pharmacological treatment of disease. For example, targeted delivery can shorten drug delivery and/or response time and also lower effective dosages of drugs, thus reducing undesired side effects which arise from elevated dosage levels.

What is needed are compositions and methods comprising molecules that home specifically to inflamed central nervous system tissue to aid in the detection of the diseased tissue and also targeting of therapeutic agents to the central nervous system to treat diseases characterized by inflammation, such as multiple sclerosis.

SUMMARY OF THE INVENTION

It is to be understood that both the foregoing general description of the invention and the following detailed description are exemplary, and thus do not restrict the scope of the invention.

In one aspect, the present invention provides isolated central nervous system-homing peptides. The peptides can be used for the investigation, detection, treatment or prevention of neuroinflammation in a subject.

In one aspect, the present invention provides an isolated central nervous system-homing peptide, wherein the peptide comprises an amino acid motif selected from the group consisting of i.
KRSS; (SEQ ID NO: 1)

ii.
RAK;

iii.
PGESS; (SEQ ID NO: 2)

iv.
SLTQ; (SEQ ID NO: 3)

v.
AMGN; (SEQ ID NO: 4)
and vi.
GDRLV. (SEQ ID NO: 5)

In another aspect, the invention provides an isolated central nervous system homing peptide, wherein the peptide comprises an amino acid sequence selected from the group consisting of i.
RGGKRSS; (SEQ ID NO: 6)

ii.
SLTQDQG; (SEQ ID NO: 7)

iii.
ADAQADV; (SEQ ID NO: 8)

ii.
RAKGRDA; (SEQ ID NO: 9)

iii.
KASRLGR; (SEQ ID NO: 10)

iv.
RGASMDG; (SEQ ID NO: 11)

v.
GRPGESS; (SEQ ID NO: 12)
and vi.
SRTEGDV. (SEQ ID NO: 13)

In another aspect, the invention provides an isolated central nervous system homing peptide, wherein the peptide comprises an amino acid sequence selected from the group consisting of i.
(SEQ ID NO: 14)
CRGGKRSSC;

ii.
(SEQ ID NO: 15)
CSLTQDQGC;

iii.
(SEQ ID NO: 16)
CADAQADVC;

iv.
(SEQ ID NO: 17)
CRAKGRDAC;

v.
(SEQ ID NO: 18)
CKASRLGRC;

vi.
(SEQ ID NO: 19)
CRGASMDGC;

vii.
(SEQ ID NO: 20)
CGRPGESSC;
and viii.
(SEQ ID NO: 21)
CSRTEGDVC.

In some embodiments, the central nervous system homing peptide consists of an amino acid sequence selected from the group consisting of i.
(SEQ ID NO: 14)
CRGGKRSSC;

ii.
(SEQ ID NO: 15)
CSLTQDQGC;

iii.
(SEQ ID NO: 16)
CADAQADVC;

iv.
(SEQ ID NO: 17)
CRAKGRDAC;

v.
(SEQ ID NO: 18)
CKASRLGRC;

vi.
(SEQ ID NO: 19)
CRGASMDGC;

vii.
(SEQ ID NO: 20)
CGRPGESSC;
and viii.
(SEQ ID NO: 21)
CSRTEGDVC.

The size of the peptide is not particularly limiting. In some embodiments, the peptide is at least 3, 4, 5, 6, 7, 8, 9, 10, 11, 12, 13, 14, 15, 16, 17, 18, 19 or 20 amino acids in length.

In another embodiment, the invention provides a method of detecting neuroinflammation in a subject, comprising administering to the subject a central nervous system homing peptide as described herein, and detecting the presence of the homing peptide in central nervous system tissue. In some embodiments, the subject is at risk or is suspected of having multiple sclerosis.

In some embodiments, the method comprises monitoring neuroinflammation in a subject over time, comprising i) administering to the subject a central nervous system homing peptide as described herein, and detecting the presence of the homing peptide in central nervous system tissue;

ii) administering to the subject a central nervous system homing peptide as described herein after a period of time subsequent to the administering and detecting steps of step i), and detecting the presence of the homing peptide in central nervous system tissue; and iii) comparing the levels of the homing peptide detected in the central nervous system tissue from steps i) and ii).

In another embodiment, the invention provides a method of screening for therapeutic effectiveness of an agent to treat neuroinflammation in a subject comprising i) obtaining the results of an assay measuring neuroinflammation in the subject, wherein the neuroinflammation is measured by administering to the subject a central nervous system homing peptide as described herein and detecting levels of the homing peptide in the central nervous system tissue; and ii) administering to the subject a therapeutic agent after the assay of step i); and iii) obtaining the results of an assay measuring neuroinflammation in the subject, wherein the neuroinflammation is measured by administering to the subject a central nervous system homing peptide as described herein and detecting levels of the homing peptide bound to the central nervous system tissue after the administering of step ii), wherein a reduction in the level of the homing peptide in the central nervous system tissue compared to the level from the subject in step i) indicates that the therapeutic agent may be effective in treating neuroinflammation in the subject.

In another embodiment, the invention provides a method of monitoring a response to a therapeutic agent to treat neuroinflammation in a subject, comprising i) administering to the subject a therapeutic agent to treat neuroinflammation;

ii) administering to a subject a homing peptide that binds to central nervous system tissue characterized by neuroinflammation; and iii) detecting the presence or the absence of the homing peptide bound to the tissue.

In another embodiment, the invention provides a method of treating neuroinflammation in a subject, comprising administering to the subject a composition comprising an effective amount of a central nervous system homing peptide as described herein in combination with an effective amount of a therapeutic agent, wherein the homing peptide facilitates the delivery of the therapeutic agent to inflamed central nervous system tissue. In some embodiments, the homing peptide is conjugated to the therapeutic agent. In some embodiments, the homing peptide is conjugated to a nanoparticle that releases the therapeutic agent.

In some embodiments, the homing peptide is conjugated to the surface of a nanoparticle. In some embodiments, the homing peptide is conjugated to the surface of a liposome.

In some embodiments, the therapeutic agent is selected from the group consisting of interferon beta-1a, glatiramer acetate, daclizumab, teriflunomide, fingolimod, dimethyl fumarate, alemtuzumab, mitoxantrone and natalizumab.

BRIEF DESCRIPTION OF THE FIGURES

The skilled artisan will understand that the drawings, described below, are for illustration purposes only. The drawings are not intended to limit the scope of the present teachings in any way.

FIG. 1. Disease model of experimental autoimmune encephalomyelitis (EAE).

FIG. 5. Peptide sequences and examples of proteins containing homologous motifs. Peptides were analyzed using NCBI protein blast database repository to identify proteins with homologous amino acid sequences or motifs. Frequency denotes the number of peptides with the same sequence/total number of peptides, number in parenthesis represent frequency as percentage, h; human and m; mouse.

FIG. 6. Eukaryotic Linear Motif (ELM) Domain Search.

FIG. 13. Binding of FITC-labeled KRSS (SEQ ID NO:1) and RAK peptide to various organs of EAE mice in peptide overlay assay. A) The binding of KRSS (SEQ ID NO:1) to the spleen, kidney, liver and lung tissue showed minimal binding. B) The binding of RAK to the spleen, kidney, liver and lung tissue showed minimal binding except for lung.

DETAILED DESCRIPTION OF THE INVENTION

Figure 2:
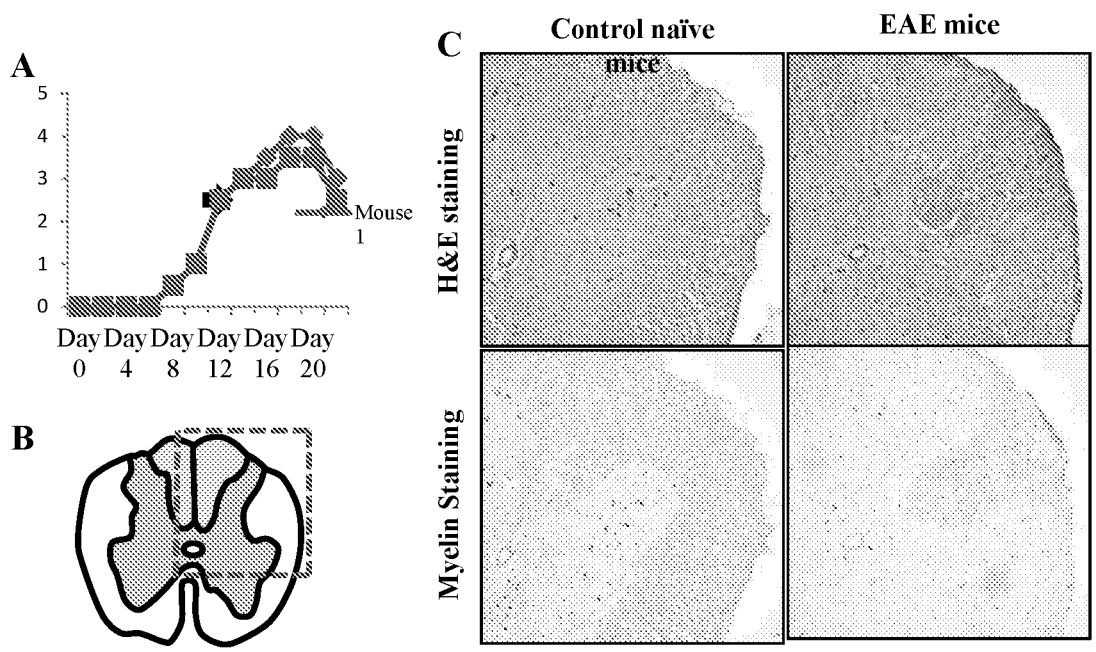
FIG. 2. Induction and evaluation of EAE in C57BL/6 mice. A: The clinical score of the animals and the pattern of disease development, Animal with clinical score of 2.5±0.5 were selected for phage screening. B: The area represented in the histology section shown in section 'C'. C: The histology of naïve (control) and EAE mice. The upper panel is H&E staining and the lower panel is myelin staining (10×). CNS-infiltrating mononuclear cells seen as blue dots were increased in EAE mice compared to normal mice (upper panel). Similarly, spinal cord demyelination was seen in EAE mice, but not in normal mice (lower panel).
Figure 3:
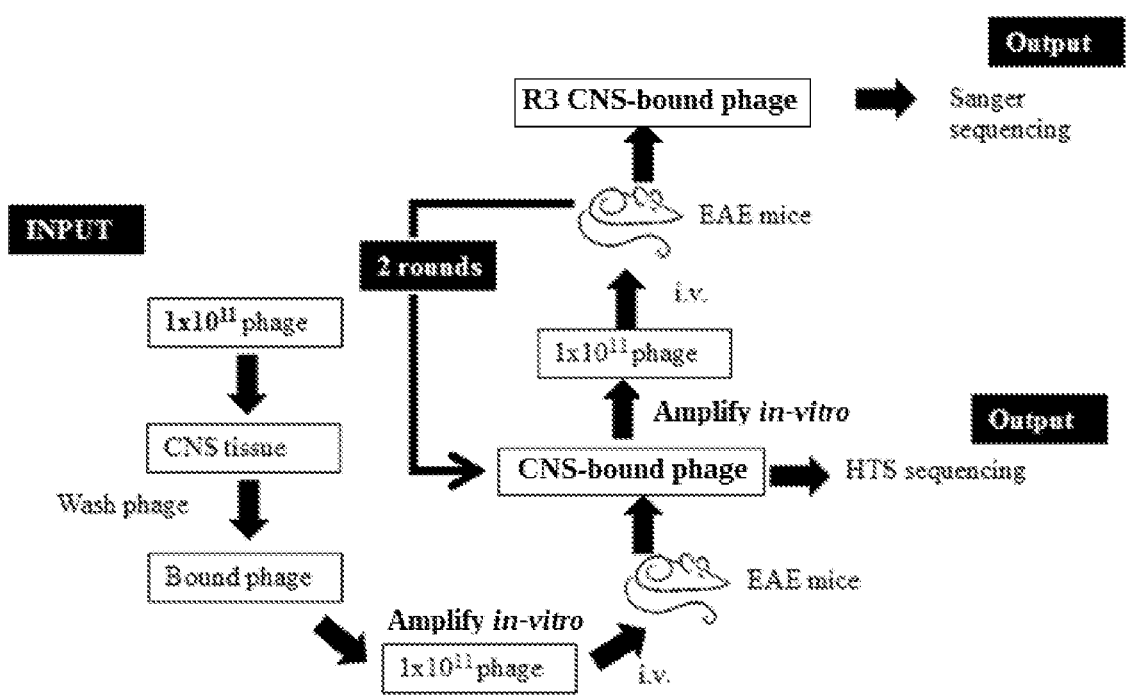
FIG. 3. A schematic plan of phage library screening. Phage ($1\times10^{11}$) were first incubated with the CNS tissue for ex-vivo screening, the unbound phage were washed off, and the bound phage were rescued using *E. coli*. Phage were amplified and equal amount of phage were injected i.v. into control and disease-bearing EAE mice having a clinical score of 2 to 3. The phage were allowed to circulate for 15 min and then the animals were euthanized, perfused extensively, and the CNS tissue was harvested. The CNS tissue was homogenized, the bound phage were rescued using *E. coli*, and the DNA samples prepared from them were subjected to HTS. The in-vivo cycle was repeated for a total of 3 times for preparing the samples for manual (Sanger) sequencing and the sequencing was performed.
Figure 4:
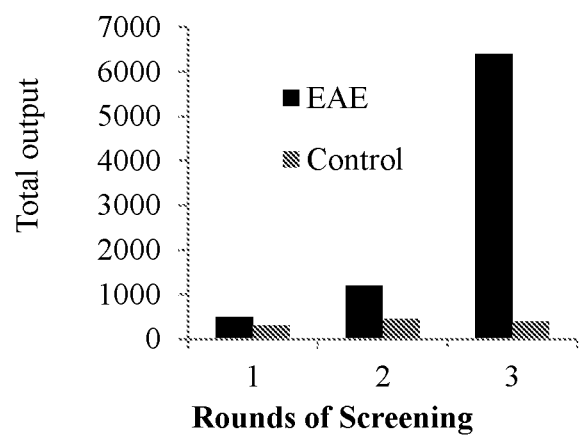
FIG. 4. Ex-vivo and in-vivo screening of CX7C phage library. Enrichment of phage clones based on manual (Sanger) sequencing method. The input for all rounds was $1\times10^{11}$. The total output was quantified using *E. coli* strain BLT5615. The enrichment obtained until round 3 in EAE mice was compared to that in control mice. Round 3 enrichment for EAE was repeated.
Figure 7:
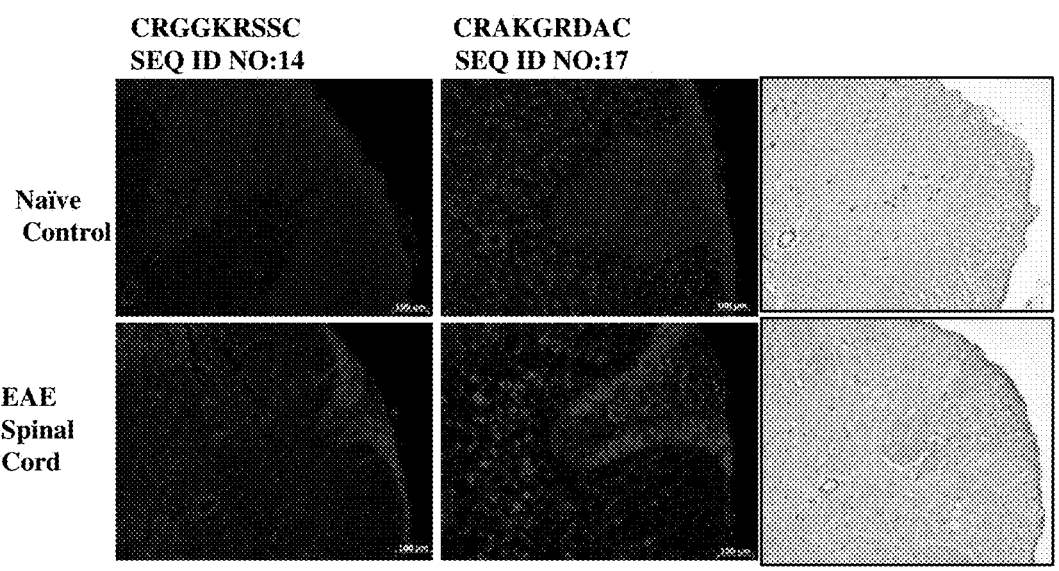
FIG. 7. Phage clone binding in paraffin sections of spinal cord in EAE and normal mice.
Figure 8:
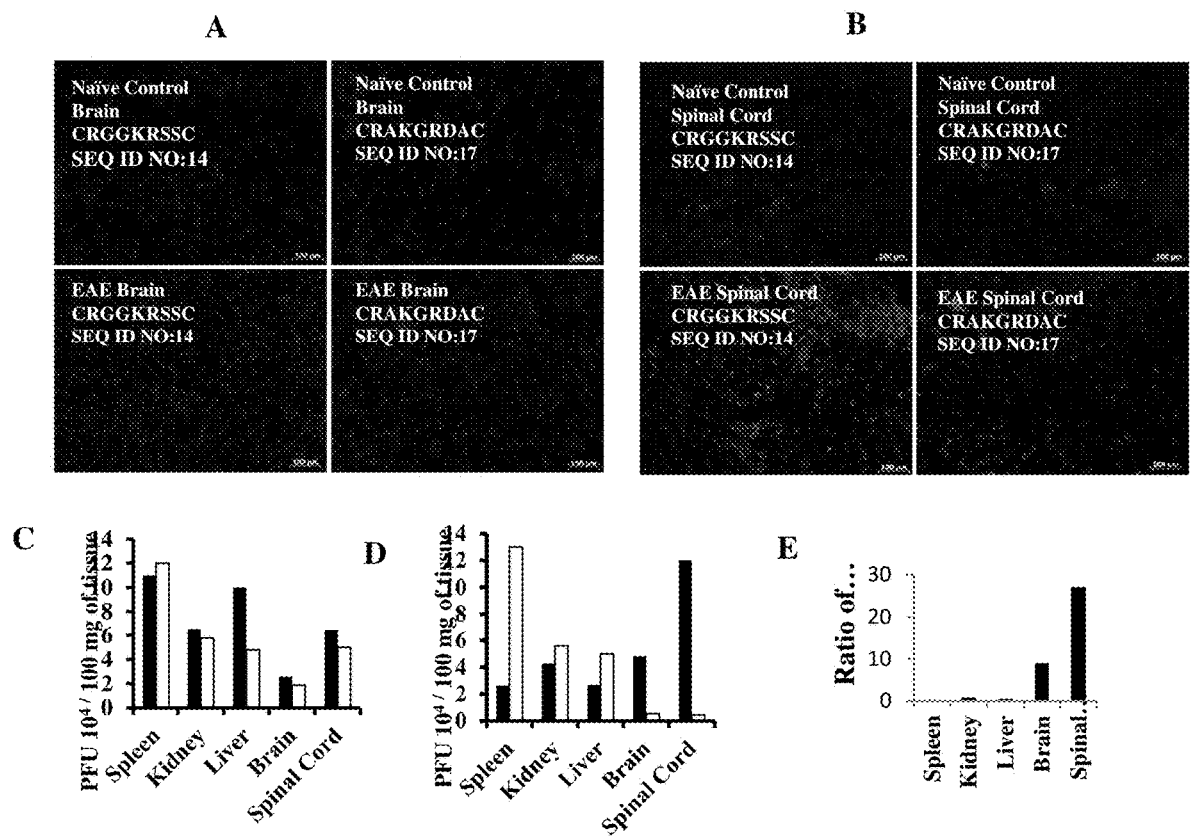
FIG. 8. Phage clones binding to CNS and other tissues. A: Phage clone binding to cryosections of the brain, B: phage clone binding to cryosections of the spinal cord. C: Biodistribution of phage CRGGKRSSC (SEQ ID NO:14) (filled bar) and CRAKGRDAC (SEQ ID NO:17) (open bar) in normal C57BL/6 mice. D: Homing of phage to different organs in the EAE mice. E: Ratio of CRGGKRSSC) (SEQ ID NO:14)/CRAKGRDAC (SEQ ID NO:17) in different organs. Phage ($1\times10^{11}$) were injected i.v. and allowed to circulate in all cases.
Figure 9:
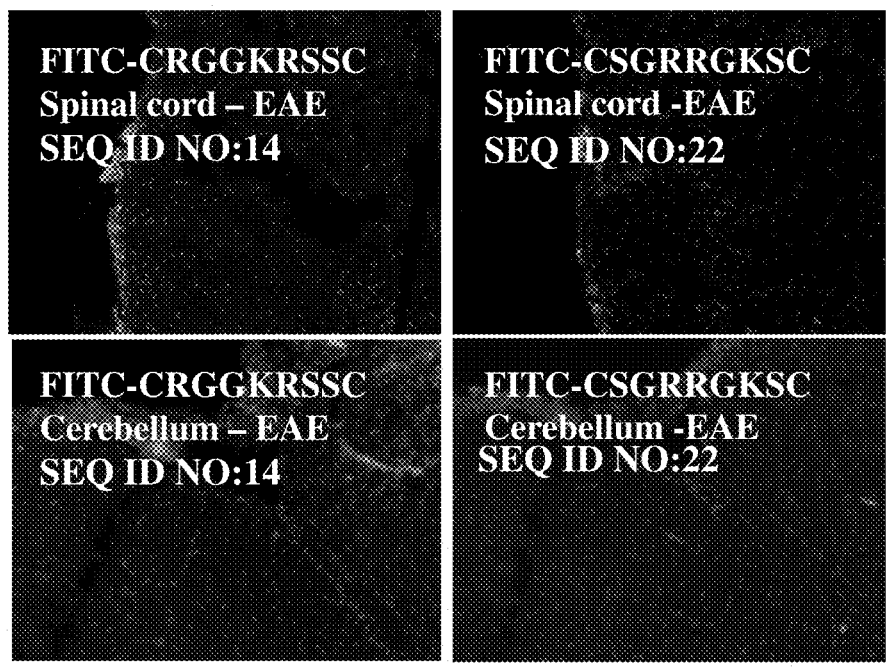
FIG. 9. FITC-labeled peptide binding. The binding of CRGGKRSSC (SEQ ID NO:14) and scramble of CRGGKRSSC (SEQ ID NO:14) aka CSGRRGKSC (SEQ ID NO:22) to spinal cord and brain cerebellum showed significantly higher binding of CRGGKRSSC (SEQ ID NO:14) to the spinal cord of EAE mice compared to scrambled peptide, both in spinal cord and cerebellum of brain.
Figure 10:
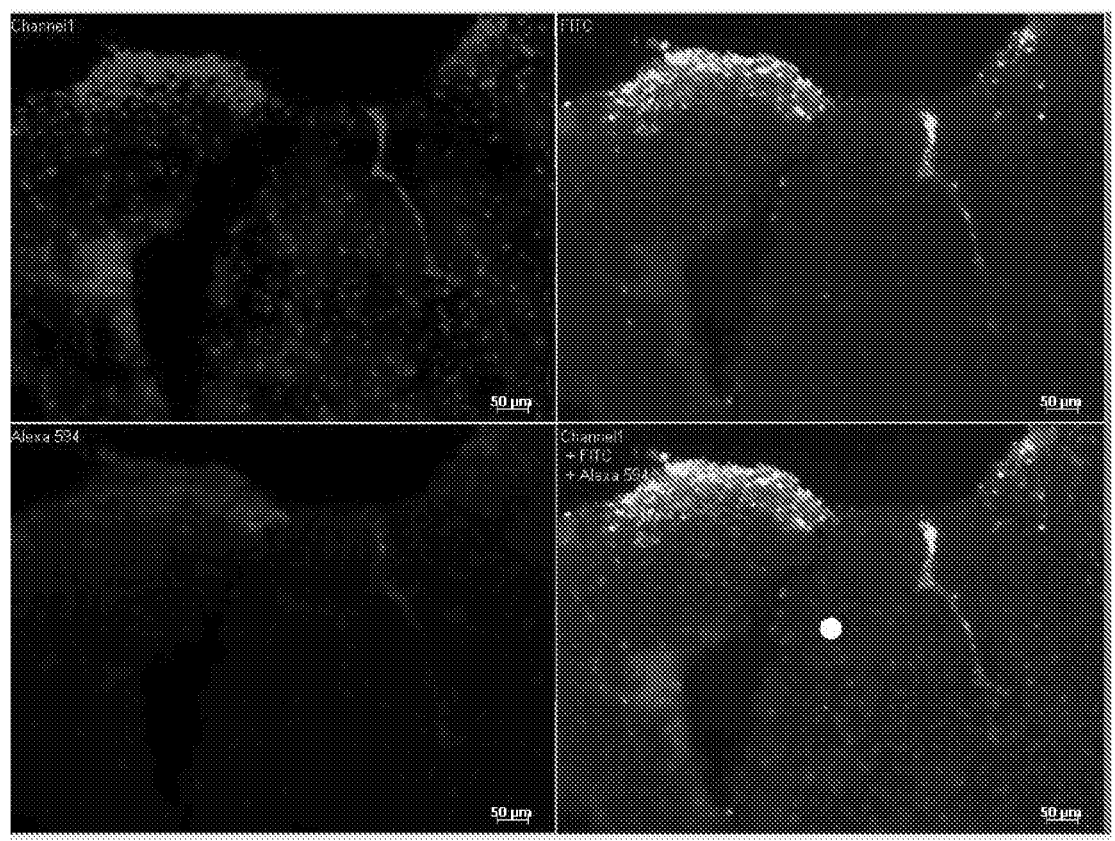
FIG. 10. Shown are images of brain cerebellum showing binding by KRSS FITC (SEQ ID NO:1) and CD-31 Alexa 594.
Figure 11:
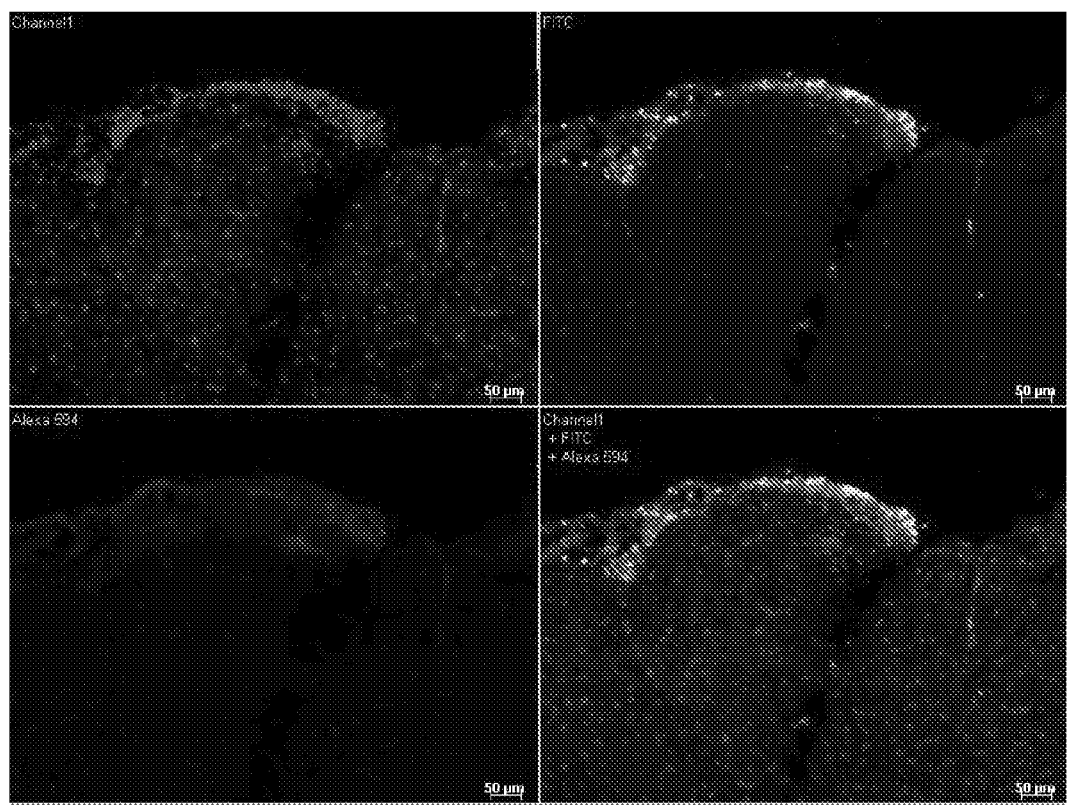
FIG. 11. Shown are images of brain cerebellum showing binding by RAK_FITC and CD-31 Alexa 594.
Figure 12:
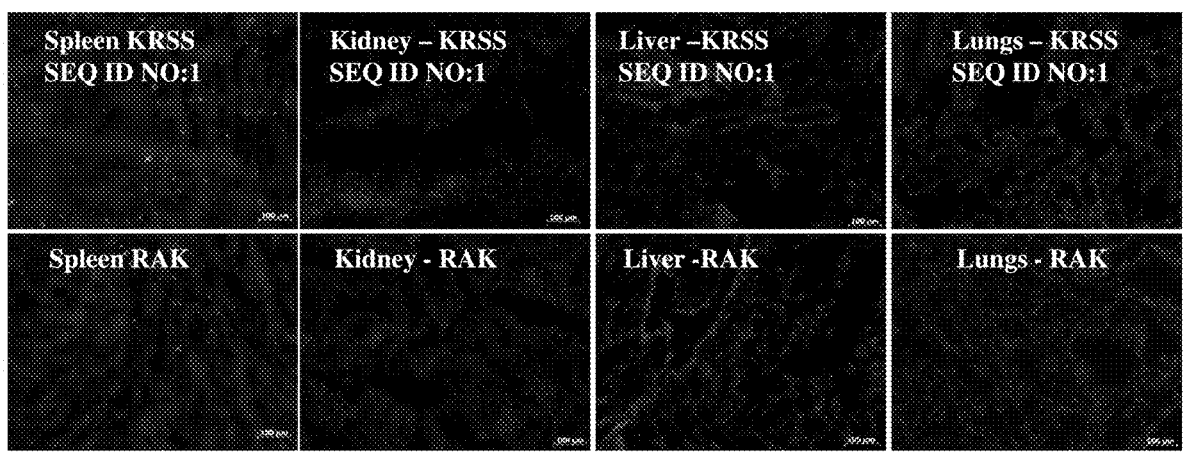
FIG. 12. Binding of FITC-labeled KRSS (SEQ ID NO:1) and RAK peptide in various organs of normal mice in peptide overlay assay. Top) The binding of KRSS (SEQ ID NO:1) to the spleen, kidney, liver and lung tissue showed minimal binding except for spleen. Bottom) The binding of RAK to the spleen, kidney, liver and lung tissue showed minimal binding.
Figure 14:
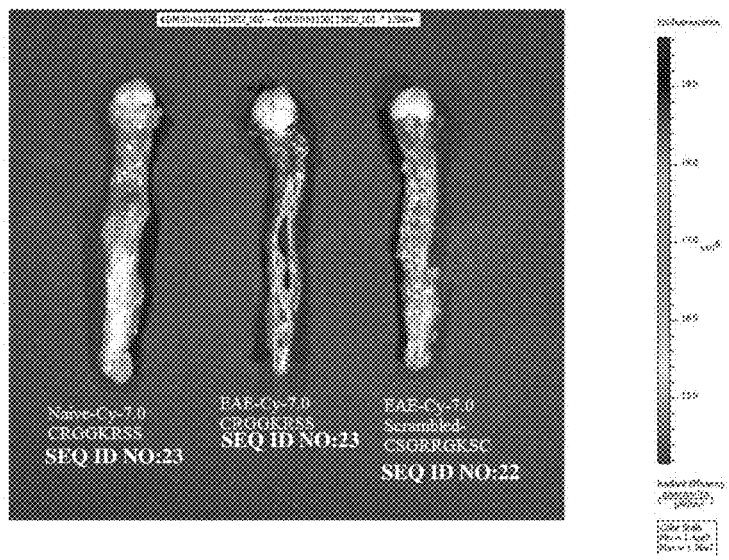
FIG. 14. Ex-vivo imaging of spinal cord inflammation in EAE mice. Near Infrared (NIRF) cyanine 7 (Cy7) dye-labeled CRGGKRSSC (SEQ ID NO:14) and control peptide was injected into the tail vein of EAE mice and naive mice. The peptides were allowed to circulate for 24 hrs and then the mice were euthanized, perfused extensively using PBS and the brain was exposed and spinal cord was removed along with the other tissues and scanned for NIRF imaging signals using IVIS Xenongen.
Figure 15:
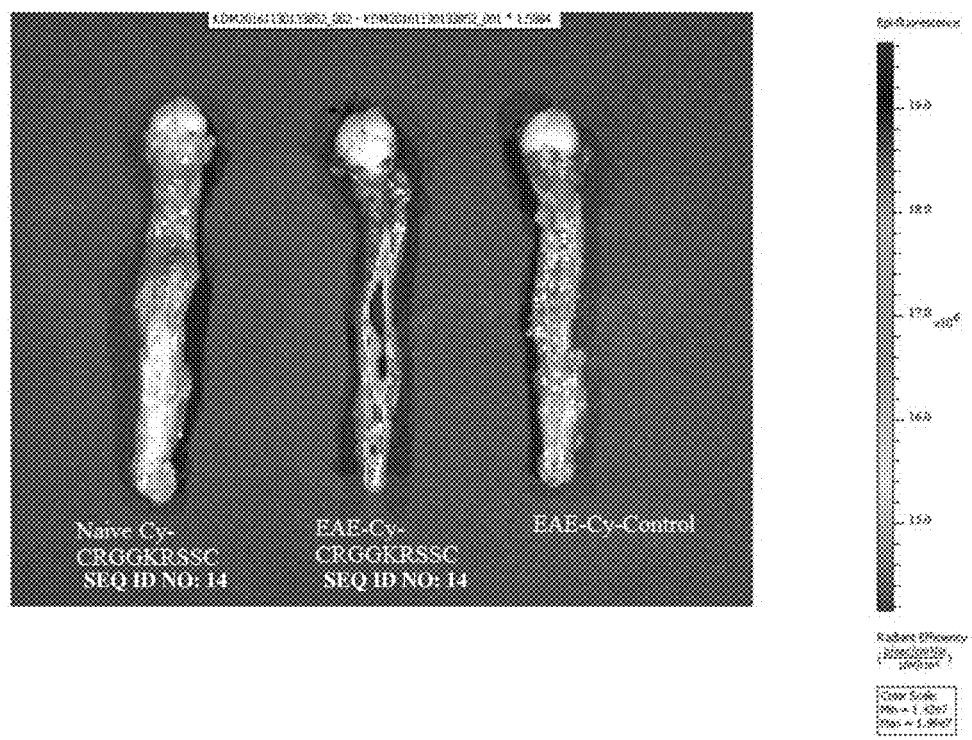
FIG. 15. Imaging of the central nervous system (the brain and spinal cord) of EAE and control mice using Cy7-labeled "KRSS" peptide (SEQ ID NO:1). Cy7-labeled peptide "KRSS" (SEQ ID NO:1) or control peptide was administered by intravenous injection into EAE mice. KRSS (SEQ ID NO:1) peptide was also injected into a naïve control mouse. Near infrared (NIR) images were taken at 24 h after peptide injection. Representative images are shown.

The present inventors hypothesized that the CNS is characterized by unique molecular markers that facilitate both selective migration of pathogenic T cells into the target organ (the CNS) as well as cellular interaction with the inducers/mediators of inflammation and tissue damage. Described herein is a molecular approach to identify novel markers in inflamed CNS. The present application describes an innovative approach of in vivo enrichment of clones from a phage peptide-display library. The advantage of the phage system for detection of tissue-specific markers is that there is no a priori bias in predicting the ligand in the CNS.

The inventors have completed a study using the mouse experimental autoimmune encephalomyelitis (EAE) model of human MS. The objective of the study was to identify unique inflamed CNS-specific markers both for monitoring the disease process and to exploit one or more of these markers for the targeting of drugs to downregulate inflammation and tissue damage in the CNS without undue adverse reactions or systemic toxicity.

The present inventors have identified several phage-encoded 9 amino acid long peptides that home specifically to inflamed CNS, particularly the spinal cord and to a lesser extent the cerebellum in mice with EAE. The results of the study help to advance the understanding of the pathogenesis of neuroinflammation, such as in multiple sclerosis, and paves the way for designing novel peptide-directed therapeutics for translational research.

Reference will now be made in detail to embodiments of the invention which, together with the drawings and the following examples, serve to explain the principles of the invention. These embodiments describe in sufficient detail to enable those skilled in the art to practice the invention, and it is understood that other embodiments may be utilized, and that structural, biological, and chemical changes may be made without departing from the spirit and scope of the present invention. Unless defined otherwise, all technical and scientific terms used herein have the same meanings as commonly understood by one of ordinary skill in the art.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. Furthermore, where the description of one or more embodiments uses the term "comprising," those skilled in the art would understand that, in some specific instances, the embodiment or embodiments can be alternatively described using the language "consisting essentially of" and/or "consisting of." As used herein, the term "about" means at most plus or minus 10% of the numerical value of the number with which it is being used.

It is contemplated that any method or composition described herein can be implemented with respect to any other method or composition described herein.

One skilled in the art may refer to general reference texts for detailed descriptions of known techniques discussed herein or equivalent techniques. These texts include *Current Protocols in Molecular Biology* (Ausubel et. al., eds. John Wiley & Sons, N.Y. and supplements thereto), *Current Protocols in Immunology* (Coligan et al., eds., John Wiley St Sons, N.Y. and supplements thereto), *Current Protocols in Pharmacology* (Enna et al., eds. John Wiley & Sons, N.Y. and supplements thereto) and *Remington: The Science and Practice of Pharmacy* (Lippincott Williams & Wilicins, 2Vt edition (2005)), for example.

Central Nervous System Homing Peptides

In one embodiment, the present invention is directed to a peptide that homes to inflamed central nervous system tissue in an animal. As described herein, a central nervous system homing peptide is any peptide that localizes to the central nervous system characterized by neuroinflammation. A central nervous system homing peptide also encompasses conjugates as described herein. In some embodiments, homing peptides are provided as individual molecules. In some embodiments, homing peptides are provided as a multimer which is a molecule comprising more than one homing peptide. In some embodiments, a combination of individual homing molecules and multimers is provided. In some embodiments, the multimer comprises homing peptides of heterogeneous amino acid sequences. In some embodiments, the multimer comprises homing peptides that have identical amino acid or substantially identical amino acid sequences.

The cause or origin of the neuroinflammation is not particularly limiting. In some embodiments, the neuroinflammation is associated with one or more of the following conditions: Parkinson's disease, multiple sclerosis, Alzheimer's disease and Huntington's disease, amyotrophic lateral sclerosis, Tay-Sachs Disease, Krabbe's Disease, Gaucher's Disease, Farber's Disease, Sandhoff's Disease, Niemann-Pick Disease, Fabry's Disease, Hurler's Syndrome, Scheie's Syndrome, Hunter's Syndrome, San Fillipo's Syndrome, Maroteaux-Lany Syndrome, Sly Syndrome, Fucosidosis, Alpha-mannosidosis, Beta-mannosidosis, Schindler's Disease, Pompeii's Disease, Woman's Disease, Infantile Neuronal Ceroid Lipofuscinosis, autism, and traumatic brain injury.

In some embodiments, the multimers allow the simultaneous interaction of more than one peptide with one or more biological entities, such as a peptide receptor molecule, or cell surface antigen or epitope. In some embodiments, the strength of such multiple interactions is much stronger than the interaction between a single peptide and a corresponding single receptor. Any suitable approach can be used to prepare homing peptide multimers of the invention. While some embodiments concern the more or less random conjugation of peptide(s) and linker(s), and represent a desirable way to rapidly generate libraries of homing peptide multimers, one embodiment of the present invention concerns the ability to control the location(s) and nature of the conjugation between homing peptide(s) and linker(s).

In one embodiment, peptides of a multimer are linked via intervening linkers ("linker" means any bond, e.g., a covalent bond, an ionic bond, and a hydrogen bond, atom, group of atoms, molecule, or group of molecules disposed between two molecules linked by the linker). "Peptide" means any synthetic or naturally occurring sequence of amino acid residues linked by peptide bonds. "Amino acid residue" refers to a residue of the amino acid after incorporation into a peptide, which incorporation results in the loss of one or more atoms from the amino acid. "Amino acid" refers to any synthetic or naturally occurring molecule comprising an amino group and a carboxylic acid group. Preferred amino acids are α-amino carboxylic acids, particularly those that are incorporated into proteins in nature. Peptides may be linked "end-to-end" (via each peptide's C or N-terminus), "end-to-sidechain," via reactive functional groups present on residues within a peptide sequence, or "side-chain-to-side chain", via reactive functional groups present on residues within a peptide sequence. In another embodiment, ends or side chain(s) of homing peptide are joined to a scaffold (a "scaffold" is any molecule that provides a molecular framework for an array of other molecules linked thereto). Either end (C or N-terminus) of a homing peptide can be coupled to the scaffold. Methods of forming multimeric peptides are described in, e.g., U.S. Pat Appl. Pub. No. 2004/0058865, which is incorporated by reference herein.

In some embodiments, the invention provides an isolated central nervous system homing peptide, wherein the peptide comprises an amino acid motif selected from the group consisting of:

i. KRSS; (SEQ ID NO: 1)

ii. RAK;

iii. PGESS; (SEQ ID NO: 2)

iv. SLTQ; (SEQ ID NO: 3)

v. AMGN; (SEQ ID NO: 4)
and vi. GDRLV. (SEQ ID NO: 5)

In another aspect, the invention provides an isolated central nervous system homing peptide, wherein the peptide comprises an amino acid sequence selected from the group consisting of i. RGGKRSS; (SEQ ID NO: 6)

ii. SLTQDQG; (SEQ ID NO: 7)

iii. ADAQADV; (SEQ ID NO: 8)

iv. RAKGRDA; (SEQ ID NO: 9)

v. KASRLGR; (SEQ ID NO: 10)

vi. RGASMDG; (SEQ ID NO: 11)

vii. GRPGESS; (SEQ ID NO: 12)
and viii. SRTEGDV. (SEQ ID NO: 13)

In some embodiments, the peptide comprises an amino acid sequence that is at least 70% identical to any of SEQ ID NOS: 6-13. In some embodiments, the peptide comprises an amino acid sequence that is at least 85% identical to any of SEQ ID NOS: 6-13. In some embodiments, the peptide is at least 70% identical to any of SEQ ID NOS: 6-13. In some embodiments, the peptide is at least 85% identical to any of SEQ ID NOS: 6-13. In some embodiments, the peptide consists of an amino acid sequence that is 100% identical to any of SEQ ID NOS: 6-13.

In another aspect, the invention provides an isolated central nervous system homing peptide, wherein the peptide comprises an amino acid sequence selected from the group consisting of i. CRGGKRSSC; (SEQ ID NO: 14)

ii. CSLTQDQGC; (SEQ ID NO: 15)

iii. CADAQADVC; (SEQ ID NO: 16)

iv. CRAKGRDAC; (SEQ ID NO: 17)

v. CKASRLGRC; (SEQ ID NO: 18)

vi. CRGASMDGC; (SEQ ID NO: 19)

vii. CGRPGESSC; (SEQ ID NO: 20)
and viii. CSRTEGDVC. (SEQ ID NO: 21)

In some embodiments, the peptide comprises an amino acid sequence that is at least 77% identical to any of SEQ ID NOS: 14-21. In some embodiments, the peptide comprises an amino acid sequence that is at least 88% identical to any of SEQ ID NOS: 14-21. In some embodiments, the peptide is at least 77% identical to any of SEQ ID NOS: 14-21. In some embodiments, the peptide is at least 85% identical to any of SEQ ID NOS: 14-21. In some embodiments, the peptide consists of an amino acid sequence that is 100% identical to any of SEQ ID NOS: 14-21.

In some embodiments, the isolated central nervous system homing peptide is not naturally occurring and comprises an amino acid sequence that does not occur in nature.

In other embodiments, the peptides of the invention comprise one or more conservative amino acid substitutions. Conservative substitutions, in which an amino acid is exchanged for another having similar properties, can be made in a compound of the invention by techniques well known by one of ordinary skill in the art. Conservative amino acid substitutions typically fall in the range of about 1 to 2 amino acid residues. Guidance in determining which amino acid residues can be substituted without activity or immunological properties can be found using computer programs well known in the art, such as DNASTAR software, or in Dayhoff et al. (1978) in Atlas of Protein Sequence and Structure (Natl. Biomed. Res. Found., Washington, D.C.). Amino acid substitutions conservative in nature are when, for example, the substituted amino acid has similar structural and/or chemical properties (including, for example, molecular weight, polarity, isoelectric point, hydrophilicity, hydrophobicity, charge, etc.) (see, for example, U.S. Pat. No. 7,098,015, which is incorporated by reference in its entirety). Examples of conservative replacements are substitution of a leucine with an isoleucine or valine, an aspartate with a glutamate, or a threonine with a serine. Specifically, amino acids are generally divided into families: (1) acidic-aspartate and glutamate; (2) basic-lysine, arginine, histidine; (3) non-polar-alanine, valine, leucine, isoleucine, proline, phenylalanine, methionine, tryptophan; (4) uncharged polar-glycine, asparagine, glutamine, cysteine, serine threonine, and tyrosine; (5) aromatic amino acids-phenylalanine, tryptophan, and tyrosine.

The size of the peptide is not limiting, provided it is capable of homing to inflamed central nervous system tissue upon administration to a subject. In some embodiments, the peptide is at least 3, 4, 5, 6, 7, 8, 9, 10, 11, 12, 13, 14, 15, 16, 17, 18, 19 or 20 amino acids in length. In some embodiments, the homing peptides employed in the present invention can be peptides ranging from about 3 amino acids to about 100 amino acids in length (and all combinations and subcombinations of ranges and specific numbers of amino acids therein). In some embodiments, the homing peptides can comprise peptides ranging from about 4 to about 20 amino acids in length. In some embodiments, the homing peptides can be about 5 to about 10 amino acids in length. In some embodiments, the homing peptides can be about 6-9 amino acids. In some embodiments, the peptides are less than about 100, about 90, about 80, about 70, about 60, about 50, about 40, about 30, about 25, about 20, about 15, or about 10 amino acids in length. The peptides may comprise D and L amino acids and mixtures of D and L amino acids, and may be comprised of all natural amino acids, all synthetic amino acids, and mixtures of natural and synthetic amino acids. The peptides can be synthesized on resins using solid phase synthetic chemistry techniques as are well known in the art, using solution phase chemistry or via recombinant techniques in which organisms such as yeast or bacteria are used to produce the peptide.

In some embodiments, the homing peptides disclosed herein can be used in diagnostic and therapeutic applications. In some embodiments, when used in therapeutic applications, the homing peptides may be administered in combination with drugs or prodrugs which are effective against a disease or condition, such as neuroinflammation. A therapeutic agent, e.g., a drug or prodrug, is any compound or formulation thereof which is effective in helping to prevent or treat a disease or condition. "Effective in helping to prevent or treat a disease or condition" indicates that administration in a clinically appropriate manner results in a beneficial effect for at least a statistically significant fraction of patients, such as an improvement of symptoms, a cure, a reduction in disease load, extension of life, improvement in quality of life, or other effect generally recognized as positive by medical doctors familiar with treating the particular type of disease or condition.

In one embodiment, the invention provides a homing peptide conjugate. As used herein, the term "conjugate" refers to a homing peptide having an amino acid sequence as described herein linked to one or more moieties. A "moiety" is used broadly to mean a physical, chemical, or biological material that is linked to a peptide. In some embodiments, the moiety can be used to facilitate detection of the peptide. In some embodiments, the moiety can be used to facilitate treatment or prevention of a disease or condition. In some embodiments, the moiety is a biologically useful moiety such as therapeutic moiety, a diagnostic moiety or a drug delivery vehicle.

In some embodiments, drug molecules, prodrug molecules, or other therapeutic agents may be linked to a homing peptide via covalent bonds or non-covalent bonds, e.g., ionic, electrostatic, or van der Waals bonds. In this way, homing peptides can serve as "molecular homing devices" for the targeting of drugs or other therapeutic agents to specific cells, tissue, or organs. A release mechanism for the drug or prodrug which coincides with the arrival of the drug or prodrug at the targeted cell or tissue may be triggered by local conditions at the diseased organ, tissue, or cells, e.g., the reversible reductive cleavage of a disulfide bond. The pendent drug or prodrug, whether released or not, acts as a therapeutic agent at the target site.

In some embodiments, the moiety can be a physical, chemical or biological material such as a drug releasing matrix, a cell, a liposome, microparticle, nanoparticle, microcapsule, a virus, micropump or other chambered microdevice, which can comprise a therapeutic agent such as a drug or prodrug, therapeutic molecule, nucleic acid encoding a therapeutic molecule, and the like and which can be used, for example, as a drug delivery system. Generally, such microdevices, should be nontoxic and, if desired, biodegradable.

In one embodiment, the moiety can be a therapeutic agent, for example, an agent used to treat neuroinflammation. Such a moiety when linked to a peptide, provides a conjugate useful for treating a neuroinflammation in a subject.

For example, in some embodiments, the homing peptide can be expressed as a fusion protein with a desired therapeutic peptide such that the homing peptide targets the grafted therapeutic peptide to inflamed central nervous system tissue. Such a desired peptide, which is grafted to the homing peptide, can be a polypeptide involved in inhibiting or preventing neuroinflammation.

In some embodiments, the moiety can be a detectable label such a radiolabel or fluorescent label. In some embodiments, the homing peptide is coupled with a label in such a way as to enable detection in the central nervous system. In some embodiments, a "label" can refer to at least one element, isotope or chemical compound to enable the detection. In some embodiments, the label can include a) isotopic labels, which may be radioactive or heavy isotopes; b) immune labels, which may be antibodies or antigens; or c) colored or fluorescent dyes. The labels may be coupled with the homing peptides at any position or at multiple positions. The coupling can be either direct or indirect. For example, the label should be capable of producing, either directly or indirectly, a detectable signal. In some embodiments, the detectable label can be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the homing peptide to the label may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982). In some embodiments, the label is a fluorescent label, such as FITC. In some embodiments, the label is near infrared (NIR) cyanine 7 (Cy7).

The distribution of homing peptides in the central nervous system can be detected by a number of techniques. In some embodiments, the homing peptides are imaged by computerized tomography. In some embodiments, the homing peptide is conjugated with imaging agents such as gadolinium or iron oxide particle for imaging of the CNS tissue by magnetic resonance imaging MRI. As the homing peptide target inflamed CNS, such conjugates can serve as good indicators of disease activity, specifically areas of inflammation. There are several forms of gadolinium-based contrast agents (GBCSs) which can be used, which includes Gadolinium-diethylenetriaminepenta-acetic acid (Gd-DTPA), PO—Gd, a gadolinium-based MR imaging contrast agent specific for MPO activity. Another imaging agent is ultra-small-particle iron oxide (USPIO). In some embodiments, the homing peptides conjugated with near-infra red dyes (e.g., Cyanine 7 (Cy7) are detected by a machine that detects near infrared emission. One such machine is IVIS Xenogen (or simply Xenogen).

The peptides and conjugates which are identified herein, can be synthesized in required quantities using routine methods of solid state peptide synthesis or can be purchased from commercial sources and a desired moiety can be linked to the peptide. Several methods useful for linking a moiety to a peptide are known in the art, depending on the particular chemical characteristics of the molecule.

A moiety such as a therapeutic or diagnostic agent can be conjugated to a peptide using, for example, carbodiimide conjugation (Bauminger and Wilchek, *Meth. Enzymol.* 70:151-159 (1980), which is incorporated herein by reference). Carbodiimides comprise a group of compounds that have the general formula R—N=C=N—R', where R and R' can be aliphatic or aromatic, and are used for synthesis of peptide bonds. The preparative procedure is simple, relatively fast, and is carried out under mild conditions. Carbodiimide compounds attack carboxylic groups to change them into reactive sites for free amino groups.

In some embodiments, the water soluble carbodiimide, 1-ethyl-3-(3-dimethylaminopropyl)carbodiimide (EDC) can be useful for conjugating a moiety to a peptide (see U.S. Patent Application Publication No. 2004/0131623).

In addition to using carbodiimides for the direct formation of peptide bonds, EDC also can be used to prepare active esters such as N-hydroxysuccinimide (NHS) ester. The NHS ester, which binds only to amino groups, then can be used to induce the formation of an amide bond with the single amino group of a moiety. The use of EDC and NHS in combination is commonly used for conjugation in order to increase yield of conjugate formation (Bauminger and Wilchek, supra, 1980).

Other methods for conjugating a moiety to a peptide can also be used. For example, sodium periodate oxidation followed by reductive alkylation of appropriate reactants can be used, as can glutaraldehyde crosslinking.

The covalent linking of homing peptides to other components of the present compositions, including therapeutic agents or drug delivery agents such as nanoparticles or liposomes can be accomplished using techniques which would be readily apparent to one of ordinary skill in the art, based on the present disclosure. For example, the homing peptides can be linked to molecules via the use of well known coupling or activation agents. As known to the skilled artisan, activating agents are generally electrophilic. This electrophilicity can be employed to elicit the formation of a covalent bond. Exemplary activating agents which may be used include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

In some embodiments, the homing peptide is conjugated to the surface of a nanoparticle. In some embodiments, the homing peptide is conjugated to the surface of a liposome. In some embodiments, the conjugation is covalent. In some embodiments, the conjugation is non-covalent.

In some embodiments, the homing peptide is first modified to add a lipid tail (forming a lipopeptide). In some embodiments, it is then mixed with four other defined lipids (named as DOPC, DOPE, Cholesterol and DSPE-(PEG)45-NH2) in the appropriate mole ratios (1:1:0.55:0.4:0.05) and dissolved in chloroform/methanol in a glass vial. In the case of fluorescence isothiocyanate (FITC)-liposome preparation, FITC (0.1 mole ratio) can be added to the peptide-lipopeptide and lipids mixture. The solvent can be removed with a thin flow of moisture-free nitrogen gas. One mL of sterile deionized water or phosphate buffer saline (PBS) can be added to the dried lipid films and the mixtures can be allowed to swell overnight at room temperature. The vials can then be vortexed for 3 min at room temperature to produce multilamellar vesicles (MLVs). MLVs can then be sonicated initially using a water bath (Branson ultrasonic bath) followed by probe sonifier (Fisher Scientific) at 100% duty cycle and 25 W output power to produce small unilamellar vesicles (SUVs). Liposomes containing FITC can then be centrifuged using an Amicon ultra centrifuge for 10 min at 5000 rpm to remove un-encapsulated FITC. A similar protocol can be followed for incorporation of a drug instead of FITC. In this case, liposomes or nanoparticles can encapsulate drugs for therapeutic use in vivo; or a dye for in-vitro binding to cells and tissue sections; as well as for tracking the liposomes/nanoparticles in-vivo.

The covalent bonds may involve crosslinking and/or polymerization. For example, crosslinking may occur in peptides which are joined by the disulfide bonds of the cystine residue. Crosslinking may be achieved, for example, by (1) adding a chemical substance (cross-linking agent) and exposing the mixture to heat, or (2) subjecting a composition to high energy radiation. A variety of crosslinking agents, or "tethers", of different lengths and/or functionalities are described, for example, in R. L. Lunbland, *Techniques in Protein Modification*, CRC Press, Inc., Ann Arbor, Mich., pp. 249-68 (1995), the disclosures of which are hereby incorporated herein by reference, in their entirety. Exemplary crosslinkers include, for example, 3,3'-dithiobis(succinimidylp-ropionate), dimethyl suberimidate, and its variations thereof, based on hydrocarbon length, and bis-N-maleimido-1,8-octane.

Methods of Using the Homing Peptides

The methods of using the central nervous system homing peptides are not limited. In one embodiment, the invention provides a method of detecting neuroinflammation in a subject, comprising administering to the subject a central nervous system homing peptide as described herein, and detecting the presence of the homing peptide in central nervous system tissue.

In some embodiments, the subject is at risk or is suspected of having multiple sclerosis.

In one embodiment, the method comprises monitoring neuroinflammation in a subject over time, comprising i) administering to the subject a central nervous system homing peptide as described herein, and detecting the presence of the homing peptide in central nervous system tissue;

ii) administering to the subject a central nervous system homing peptide as described herein after a period of time subsequent to the administering and detecting steps of i), and detecting the presence of the homing peptide in central nervous system tissue; and iii) comparing the levels of the homing peptide in the central nervous system tissue from steps i) and ii). In some embodiments, an increase in the level of the homing peptide in the central nervous system tissue indicates an increase in neuroinflammation over time, and a reduction in the level of the homing peptide in the central nervous system tissue indicates a reduction in neuroinflammation over time.

In one embodiment, the invention provides a method of screening for therapeutic effectiveness of an agent to treat neuroinflammation in a subject comprising i) obtaining the results of an assay measuring neuroinflammation in the subject, wherein the neuroinflammation is measured by administering to the subject a central nervous system homing peptide as described herein and detecting levels of the homing peptide in the central nervous system tissue; and ii) administering to the subject an amount of a therapeutic agent after the assay of step i); and iii) obtaining the results of an assay measuring neuroinflammation in the subject, wherein the neuroinflammation is measured by administering to the subject a central nervous system homing peptide as described herein and detecting levels of the homing peptide in the central nervous system tissue after the administering of step ii), wherein a reduction in the level of the detected homing peptide in the central nervous system tissue compared to the level of the detected homing peptide in the central nervous system tissue from the subject in step i) indicates that the drug may be effective in treating neuroinflammation in the subject.

In one embodiment, the invention provides a method of monitoring a response to a therapeutic to treat neuroinflammation in a subject, comprising administering to the subject an effective amount of a therapeutic to treat neuroinflammation; administering to a subject a homing peptide that binds to central nervous system tissue characterized by neuroinflammation, and detecting the presence or the absence of the homing peptide bound to the tissue. In some embodiments, an increase or no change in the level of the homing peptide in the central nervous system tissue indicates that the therapeutic is ineffective in the treatment of neuroinflammation, and a reduction in the level of the homing peptide in the central nervous system tissue indicates a reduction in neuroinflammation, and effectiveness of the therapeutic.

In another embodiment, the invention is further directed to a method of treating neuroinflammation in a subject, comprising administering to the subject a composition comprising an effective amount of a central nervous system homing peptide as described herein in combination with an effective amount of a therapeutic agent, wherein the homing peptide facilitates the delivery of the therapeutic agent to inflamed central nervous system tissue. In some embodiments, the homing peptide is conjugated to the therapeutic agent. In some embodiments, the homing peptide is conjugated to a nanoparticle or liposome that releases the therapeutic agent.

In some embodiments, the neuroinflammation is associated with one or more of the following conditions: Parkinson's disease, multiple sclerosis, Alzheimer's disease and Huntington's disease, amyotrophic lateral sclerosis, Tay-Sachs Disease, Krabbe's Disease, Gaucher's Disease, Farber's Disease, Sandhoff's Disease, Niemann-Pick Disease, Fabry's Disease, Hurler's Syndrome, Scheie's Syndrome, Hunter's Syndrome, San Fillipo's Syndrome, Maroteaux-Lany Syndrome, Sly Syndrome, Fucosidosis, Alpha-mannosidosis, Beta-mannosidosis, Schindler's Disease, Pompeii's Disease, Woman's Disease, Infantile Neuronal Ceroid Lipofuscinosis, autism, and traumatic brain injury.

As used herein, the term "pharmacologically effective dose" or an "effective amount" (or a derivative or variation thereof) is an amount of a peptide of the invention or composition containing the same that alleviates, totally or partially, neuroinflammation in a subject or a subject at risk of developing neuroinflammation. Unless otherwise indicated when referring to the administration of a peptide of the invention or composition containing the same, said peptide of the invention or composition containing the same is administered at a concentration that is a pharmacologically effective dose. A pharmacologically effective dose will depend upon, for example, subject size, gender, magnitude of the associated disease, condition, or injury, and genetic or non-genetic factors associated individual pharmacokinetic or pharmacodynamic properties of the administered peptide of the invention or composition containing the same. For a given subject in need thereof, a pharmacologically effective dose can be determined by one of ordinary skill in the art and by methods known to one of ordinary skill in the art.

As used herein, the term "subject" refers to any recipient of the peptides or therapeutic compositions comprising the same, as described herein. In some embodiments, the subject is a mammal, such as a rat, mouse, human, cat, dog, monkey, chimpanzee, gorilla, cow, or horse.

Compositions

The present invention is further directed to a composition comprising an isolated central nervous system homing peptide described herein. The compositions as described herein can be used in any of the methods as described herein. In one embodiment, the invention provides a composition comprising an isolated central nervous system homing peptide conjugated to a detectable label. In another embodiment, the invention provides a composition comprising an isolated central nervous system homing peptide and a therapeutically active agent, which can include a drug or prodrug, wherein the peptide and the agent are not covalently coupled or non-covalently associated with each other. In some embodiments, the peptide and the therapeutically active agent are covalently bound to each other. In some embodiments, the composition comprises an isolated central nervous system homing peptide conjugated to a detectable label and a therapeutically active agent.

In some embodiments, the therapeutically active agent is a prodrug. Prodrugs include chemical derivatives of a biologically-active parent compound which, upon administration, will eventually liberate the active parent compound in vivo. Use of prodrugs can allow the artisan to modify the onset and/or duration of action in vivo. In addition, the use of prodrugs can modify the transportation, distribution or solubility of a drug in the body. Furthermore, prodrugs may reduce the toxicity and/or otherwise overcome difficulties encountered when administering pharmaceutical preparations.

In some embodiments, the composition comprising the isolated central nervous system homing peptide and therapeutically active agent may be used to treat a variety of conditions associated with inflammation of the central nervous system. Thus, in some embodiments, the composition can be directed to selectively target and deliver a therapeutically active agent to inflamed central nervous system tissue.

In some embodiments, the therapeutically active agent is an anti-inflammatory agent. In some embodiments, the anti-inflammatory agent includes but is not limited to steroids, such as cortisone, glucocorticoids, prednisone, prednisolone, hydrocortisone (Cortisol), cortisone acetate, methylprednisolone, dexamethasone, betamethasone, triamcinolone, beclometasone, and fludrocortisone acetate; non-steroidal anti-inflammatory drug (NSAIDs), ibuprofen, naproxen, meloxicam, etodolac, nabumetone, sulindac, tolementin, choline magnesium salicylate, diclofenac, diflusinal, indomethicin, ketoprofen, oxaprozin, piroxicam, and nimesulide, salicylates, aspirin (acetylsalicylic acid), diflunisal, salsalate, p-amino phenol derivatives, paracetamol, phenacetin, propionic acid derivatives, fenoprofen, flurbiprofen, oxaprozin, loxoprofen, acetic acid derivatives, indomethacin, sulindac, etodolac, ketorolac, nabumetone, enolic acid (oxicam) derivatives, piroxicam, meloxicam, tenoxicam, droxicam, lornoxicam, isoxicam, fenamic acid derivatives (fenamates), mefenamic acid, meclofenamic acid, flufenamic acid, tolfenamic acid, selective COX-2 inhibitors (coxibs), celecoxib, rofecoxib, valdecoxib, parecoxib, lumiracoxib, etoricoxib, firocoxib, sulphonanilides, nimesulide, licofelone and combinations thereof.

In some embodiments, the therapeutically active agent is selected from interferon beta, glatiramer acetate, daclizumab, teriflunomide, fingolimod, dimethyl fumarate, alemtuzumab, mitoxantrone, natalizumab and combinations thereof.

In some embodiment, natural plant-derived products, e.g., traditional medicine herbs and their products, e.g., celastrol, can serve as therapeutic agents.

In some embodiments, the compositions can be formulated to comprise a liposome, a vesicle, a nanoparticle and combinations thereof. In some embodiments, the liposome or nanoparticle can be coated with or attached on its surface with one or more peptides described herein so as to selectively target sites of interest for specific therapeutic or diagnostic purposes. In some embodiments, the liposome, vesicle, or nanoparticle is capable of releasing the therapeutic agent.

Pharmaceutical compositions of the present invention may be administered by any means that results in the contact of the therapeutic agent with the agent's site or site(s) of action in the body of a patient. The compositions may be administered by any conventional means available for use in conjunction with pharmaceuticals, either as individual therapeutic agents or in a combination of therapeutic agents. For example, the present pharmaceutical compositions may be administered alone, or they may be used in combination with other therapeutically active ingredients.

The central nervous system homing peptides are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosures of which are hereby incorporated herein by reference, in their entirety.

Pharmaceutical compositions of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The pharmaceutical compositions may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compositions may be used in the form of ingestible tablets, buccal tablets, troches, capsules, elixirs, suspensions, syrups, wafers, and the like. The amount of bioactive agent(s) in such therapeutically useful compositions is preferably such that a suitable dosage will be obtained.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The pharmaceutical compositions may also be administered parenterally or intraperitoneally. Suitable compositions may be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the pharmaceutical compositions in the required amounts, in the appropriate solvent, with various of the other ingredients enumerated above, as required, followed by filtered sterilization. Generally, dispersions may be prepared by incorporating the compositions into a sterile vehicle which contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

The dosage of the pharmaceutical compositions of the present invention that will be most suitable for prophylaxis or treatment will vary with the form of administration, the particular bioactive agent chosen and the physiological characteristics of the particular patient under treatment. Generally, small dosages may be used initially and, if necessary, increased by small increments until the desired effect under the circumstances is reached. Generally speaking, oral administration may require higher dosages.

All publications herein are incorporated by reference to the same extent as if each individual publication or patent application was specifically and individually indicated to be incorporated by reference.

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLES

Example 1—Isolation of Central Nervous System Homing Peptides Using Phage Display $1 \times 10^{11}$ phage were first incubated with tissues from CNS for ex-vivo screening, unbound phages were washed off and bound phages were rescued using *E. coli* host strain of BLT5403. Phages were amplified and equal amount of phage were injected i.v. in control and disease bearing mice with score of 2 to 3. The phages were allowed to circulate for 15 min and animals were euthanized, perfused extensively and CNS tissues were harvested. The CNS tissues were homogenized and bound phages were rescued using *E. coli* and the DNA sample was prepared and sent for HTS sequencing. The in-vivo cycle was repeated total of 3 times for manual sequencing and sequencing was performed.

Materials and Methods

Phage Vector

T7415-1b phage vectors displaying CX7C peptides, where C is cysteine and X is any amino acid residue, designed to display a constrained cyclic loop within the pIII capsid protein, were obtained from Dr. Erkki Ruolashti and Dr. Tambet Teesalu (Sanford Burnham Preybus, San Diego) via arrangement between the two institutes. These vectors had a diversity of $1.28 \times 10^9$ plaque forming unit (pfu). For amplification of vectors and plaque assay, host strains of *E. coli*, BLT5403 and BLT5615 respectively were used.

Animal Model

The antigen was prepared by emulsifying the myelin oligodendrocyte glycoprotein (MOG) region of 35-55 peptide sequence with at least >98% purity based on mass spectrophotometry (CS Bio, CA, USA) with an equal volume of complete Freund's adjuvant (CFA) containing 5 mg/ml of heat killed desiccated *M. tuberculosis*-H37RA (Bacto, MI, USA). The suspension was thoroughly mixed to form a thick emulsion. Experimental autoimmune encephalomyelitis (EAE), which closely resembles human multiple sclerosis (MS) was induced in C57BL/6 mice by subcutaneous injection of 200 μg/MOG/mouse. In addition, 2 doses of 200-400 ng each of Pertussis toxin (Calbiochem, CA, USA) were administered i.p. after MOG injection at 0 and 48 hours.

Ex-Vivo and In-Vivo Screening of Phage Library

For ex-vivo screening, CNS (brain and spinal cord) tissues were harvested from normal and EAE mice after extensive perfusion. A cell suspension, which is equivalent to 100 μg of tissue, was incubated with phages ($1 \times 10^{11}$) at 4° C. for 1 hour. After incubation, the cell suspension was washed to remove unbound phage and the bound-phage were rescued using BLT 5403 strain of *E. coli* bacteria. The phage were then amplified and equal number of phage ($1 \times 10^{11}$) were injected i.v into EAE mice with clinical score between 2 to 3. The phage were circulated in-vivo for 15 min thereafter, animals were euthanized, re-perfused, CNS tissues were collected, homogenized and phage were rescued. The phage were amplified using BLT 5403 and purified using Polyethylene glycol (PEG)-NaCl concentration to 100 μl volume. 4 ul of which were used for PCR amplification (Quiagen HotStar Taq DNA polymerase) along with DNTP (Invitrogen, USA) and primers at 5 pmol/ul (T7 super up and T7superdown). The inserts were verified using agarose gel electrophoresis. The DNA concentration was measured using nanodrop and the samples were sent for high throughput sequencing (HTS) at the core facility of Institute for Genome Sciences (IGS) at the University of Maryland (UMB) School Of Medicine. For manual Sanger sequencing, two additional rounds of in-vivo panning were performed and the clones were picked randomly from $3^{rd}$ round of in-vivo CNS samples and sent for sequencing at JHU sequencing facility.

Amplicon HTS Sequencing

To analyze the distribution of inserts from the random phage peptide library sequences, HTS sequencing was performed employing Illumina sequencing using library construction and analysis, which were carried out at IGS, UMB. DNA libraries with molecular barcode indices were constructed for sequencing on the Illumina platform using DNA Sample Prep, targeting a size of 190 bp. The amplicons were directly processed for library preparation without DNA shearing step. Raw data was processed and the sequences thus obtained were processed to trim the recognition sites and then clustered at 100% identity. A list of all the clones for each sample was created.

Bioinformatics Analysis of the Sequences

Each nucleotide sequence was translated into corresponding amino acid peptide sequence, which were analyzed for ratio with normal controls. A motif search using Parser analysis was carried out to rule out confirmation bias. A list of top 20 candidate peptides was further subjected to a homologous protein motif search using NCBI blast search. Additionally, a eukaryotic linear motif search was carried out through using EMBL Enterprise Management GmbH software.

Testing of Phage Clone Binding

A list of candidate sequences was prepared by analyzing the large number of candidate sequences, manual sequencing and bioinformatics. The clones corresponding to the candidate's sequences were amplified using single clone amplification employing bacterial host strains BLT5403. Tissues sections (cryo-sections and paraffin sections) of the brain and spinal cord were first blocked with 1% Bovine Serum Albumin (BSA) in PBS at room temperature for 30 min, which were then incubated with phage clones)($1 \times 10^{10}$) for 1 hr at 4° C., washed, and incubated with non-commercial anti-T7 rabbit antibody (1 mg/ml) for 2 hr at 4° C. and washed with PBS. The sections were then incubated with anti-Rabbit Alexa 549 (Cell Signaling, USA) for 1 hr at 4° C. The sections were washed and fixed with 4% paraformaldehyde (PFA) and stained with a nucleus-staining dye (Hoechst 33342) and mounted with Everbrite mounting medium (Biotium, USA) to protect photobleaching.

Synthesis of Peptides and Conjugation with FITC

The peptide sequences were synthesized by Genscript (NJ, USA) with at least 95% purity. For fluorescent peptides, fluorescein isothiocyanate (FITC) dye was conjugated at the amino terminus of peptides. The excitation/emission wavelengths for FITC were 490/520 nm.

Example 2—In Vivo Imaging of EAE Mice Using Central Nervous System (CNS)—Homing Peptides that were Originally Identified by Phage Library Screening The previous results of in vivo phage library screening in EAE mice showed that certain phage clones were enriched in the central nervous system (CNS) of EAE mice. The peptides encoded by these phage clones included peptide CRGGKRSSC (SEQ ID NO:14) (denoted as "KRSS" (SEQ ID NO:1)). The goal of this experiment was to determine the in vivo homing property of the KRSS (SEQ ID NO:1) peptide in EAE mice compared with control mice. For this purpose, peptide KRSS (SEQ ID NO:1) was conjugated with a dye, Cy7, which can be detected in vivo by an equipment known as Xenogen. Furthermore, the homing profile of KRSS (SEQ ID NO:1) was compared with a control peptide labeled with Cy7.

Methods

Near Infrared (NIR) Cyanine 7 (Cy7) dye-labeled test peptide CRGGKRSSC (SEQ ID NO:14) or control peptide was injected into the tail vein of diseased (EAE) mice and naive (control) mice. The peptides were allowed to circulate for 24 hours. Thereafter, mice were euthanized, perfused extensively through the heart using PBS. Following that, the brain and spinal cord were removed and scanned for NIR imaging signals using IVIS Xenogen imaging System.

Results

KRSS-Cy7 (SEQ ID NO:1) showed significantly higher accumulation in the spinal cord of EAE mice compared to control mice (See Figures). The latter barely showed any detectable signal. Furthermore, EAE mice injected with a control-Cy7 peptide also failed to display any detectable signal when compared with EAE mice injected with KRSS-Cy7 (SEQ ID NO:1). Similar results, but much lower in intensity, were observed when cerebellum of above groups of mice was examined. However, no signal was detected in the cerebrum.

Discussion

These results show that peptide KRSS (SEQ ID NO:1) when injected into the bloodstream preferentially homed to inflamed spinal cord of EAE mice but not in normal mice. This peptide can be exploited further for targeted drug delivery in EAE mice, and by extrapolation, in patients with multiple sclerosis and similar neuroinflammatory conditions of the CNS. In addition, this peptide can also be of utility for imaging of CNS in EAE/MS.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

We claim:

1. An isolated central nervous system homing peptide, wherein the peptide comprises an amino acid sequence selected from the group consisting of i. RGGKRSS; (SEQ ID NO: 6)

ii. SLTQDQG; (SEQ ID NO: 7)

iii. ADAQADV; (SEQ ID NO: 8)

iv. RAKGRDA; (SEQ ID NO: 9)

v. KASRLGR; (SEQ ID NO: 10)

vi. RGASMDG; (SEQ ID NO: 11)

vii. GRPGESS; and (SEQ ID NO: 12)

viii. SRTEGDV. (SEQ ID NO: 13)

2. The isolated central nervous system homing peptide of claim 1, wherein the peptide comprises an amino acid sequence selected from the group consisting of i. CRGGKRSSC; (SEQ ID NO: 14)

ii. CSLTQDQGC; (SEQ ID NO: 15)

iii. CADAQADVC; (SEQ ID NO: 16)

iv. CRAKGRDAC; (SEQ ID NO: 17)

v. CKASRLGRC; (SEQ ID NO: 18)

vi. CRGASMDGC; (SEQ ID NO: 19)

-continued vii.
CGRPGESSC; (SEQ ID NO: 20)
and viii.
CSRTEGDVC. (SEQ ID NO: 21)

3. A composition comprising the isolated central nervous system homing peptide of claim 1.

4. The composition of claim 3, wherein the isolated central nervous system homing peptide is conjugated to one or more moieties.

5. The composition of claim 4, wherein the moiety facilitates detection of the isolated central nervous system homing peptide.

6. The composition of claim 5, wherein the moiety is a detectable label selected from the group consisting of an isotopic label, an immune label, colored dye, fluorescent dye, and combinations thereof.

7. The composition of claim 4, wherein the moiety is an imaging agent.

8. The composition of claim 7, wherein the imaging agent is a gadolinium or iron oxide particle for imaging of the central nervous system tissue by magnetic resonance imaging.

9. The composition of claim 8, wherein the imaging agent is gadolinium-diethylenetriaminepenta-acetic acid (Gd-DTPA).

10. The composition of claim 4, wherein the moiety is a therapeutic moiety that treats or prevents a disease or condition.

11. The composition of claim 10, wherein the therapeutic moiety is an anti-inflammatory agent.

12. The composition of claim 4, wherein the moiety is a diagnostic or drug delivery vehicle.

13. The composition of claim 12, wherein the moiety comprises a particle.

14. The composition of claim 12, wherein the moiety is selected from a liposome, a vesicle, a nanoparticle, a microparticle and combinations thereof.

15. The composition of claim 14, wherein the liposome, vesicle, nanoparticle or microparticle further comprises a therapeutic agent.

16. The composition of claim 15, wherein the therapeutic agent is capable of being released from the liposome, vesicle, nanoparticle or microparticle.

17. The composition of claim 15, wherein the therapeutic agent is conjugated to the surface of the liposome, vesicle, nanoparticle or microparticle.

18. A method of detecting neuroinflammation in a subject, comprising administering to the subject a central nervous system homing peptide according to claim 1 or a composition comprising said homing peptide, and detecting the presence of the homing peptide in central nervous system tissue.

19. A method of monitoring neuroinflammation in a subject over time, comprising
  i) administering to the subject a central nervous system homing peptide according to claim 1 or a composition comprising said homing peptide, and detecting the presence of the homing peptide in central nervous system tissue;
  ii) administering to the subject a central nervous system homing peptide according to claim 1 or a composition comprising said homing peptide after a period of time subsequent to the administering and detecting steps of step i), and detecting the presence of the homing peptide in central nervous system tissue; and
  iii) comparing the levels of the homing peptide detected in the central nervous system tissue from steps i) and ii).

20. A method of screening for therapeutic effectiveness of an agent to treat neuroinflammation in a subject comprising
  i) obtaining the results of an assay measuring neuroinflammation in the subject, wherein the neuroinflammation is measured by administering to the subject a central nervous system homing peptide according to claim 1 or a composition comprising said homing peptide and detecting levels of the homing peptide in the central nervous system tissue; and
  ii) administering to the subject a therapeutic agent after the assay of step i); and
  iii) obtaining the results of an assay measuring neuroinflammation in the subject, wherein the neuroinflammation is measured by administering to the subject a central nervous system homing peptide according to claim 1 or a composition comprising said homing peptide and detecting levels of the homing peptide in the central nervous system tissue after the administering of step ii), wherein a reduction in the level of the homing peptide in the central nervous system tissue compared to the level from the subject in step i) indicates that the therapeutic agent may be effective in treating neuroinflammation in the subject.

21. A method of monitoring a response to a therapeutic agent to treat neuroinflammation in a subject, comprising
  i) administering to the subject a therapeutic agent to treat neuroinflammation;
  ii) administering to a subject a homing peptide according to claim 1 or a composition comprising said homing peptide that binds to central nervous system tissue characterized by neuroinflammation; and
  iii) detecting the presence or the absence of the homing peptide bound to the tissue.

* * * * *

SEQUENCE LISTING

```
<160> NUMBER OF SEQ ID NOS: 24

<210> SEQ ID NO 1
<211> LENGTH: 4
<212> TYPE: PRT
<213> ORGANISM: Artificial sequence
<220> FEATURE:
<223> OTHER INFORMATION: peptide

<400> SEQUENCE: 1

Lys Arg Ser Ser
1

<210> SEQ ID NO 2
<211> LENGTH: 5
<212> TYPE: PRT
<213> ORGANISM: Artificial sequence
<220> FEATURE:
<223> OTHER INFORMATION: peptide

<400> SEQUENCE: 2

Pro Gly Glu Ser Ser
1               5

<210> SEQ ID NO 3
<211> LENGTH: 4
<212> TYPE: PRT
<213> ORGANISM: Artificial sequence
<220> FEATURE:
<223> OTHER INFORMATION: peptide

<400> SEQUENCE: 3
```

Ser Leu Thr Gln
1

<210> SEQ ID NO 4
<211> LENGTH: 4
<212> TYPE: PRT
<213> ORGANISM: Artificial sequence
<220> FEATURE:
<223> OTHER INFORMATION: peptide

<400> SEQUENCE: 4

Ala Met Gly Asn
1

<210> SEQ ID NO 5
<211> LENGTH: 5
<212> TYPE: PRT
<213> ORGANISM: Artificial sequence
<220> FEATURE:
<223> OTHER INFORMATION: peptide

<400> SEQUENCE: 5

Gly Asp Arg Leu Val
1               5

<210> SEQ ID NO 6
<211> LENGTH: 7
<212> TYPE: PRT
<213> ORGANISM: Artificial sequence
<220> FEATURE:
<223> OTHER INFORMATION: peptide

<400> SEQUENCE: 6

Arg Gly Gly Lys Arg Ser Ser
1               5

<210> SEQ ID NO 7
<211> LENGTH: 7
<212> TYPE: PRT
<213> ORGANISM: Artificial sequence
<220> FEATURE:
<223> OTHER INFORMATION: peptide

<400> SEQUENCE: 7

Ser Leu Thr Gln Asp Gln Gly
1               5

<210> SEQ ID NO 8
<211> LENGTH: 7
<212> TYPE: PRT
<213> ORGANISM: Artificial sequence
<220> FEATURE:
<223> OTHER INFORMATION: peptide

<400> SEQUENCE: 8

Ala Asp Ala Gln Ala Asp Val
1               5

<210> SEQ ID NO 9
<211> LENGTH: 7
<212> TYPE: PRT
<213> ORGANISM: Artificial sequence
<220> FEATURE:
<223> OTHER INFORMATION: peptide

<400> SEQUENCE: 9

Arg Ala Lys Gly Arg Asp Ala
1               5

<210> SEQ ID NO 10
<211> LENGTH: 7
<212> TYPE: PRT
<213> ORGANISM: Artificial sequence
<220> FEATURE:
<223> OTHER INFORMATION: peptide

<400> SEQUENCE: 10

Lys Ala Ser Arg Leu Gly Arg
1               5

<210> SEQ ID NO 11
<211> LENGTH: 7
<212> TYPE: PRT
<213> ORGANISM: Artificial sequence
<220> FEATURE:
<223> OTHER INFORMATION: peptide

<400> SEQUENCE: 11

Arg Gly Ala Ser Met Asp Gly
1               5

<210> SEQ ID NO 12
<211> LENGTH: 7
<212> TYPE: PRT
<213> ORGANISM: Artificial sequence
<220> FEATURE:
<223> OTHER INFORMATION: peptide

<400> SEQUENCE: 12

Gly Arg Pro Gly Glu Ser Ser
1               5

<210> SEQ ID NO 13
<211> LENGTH: 7
<212> TYPE: PRT
<213> ORGANISM: Artificial sequence
<220> FEATURE:
<223> OTHER INFORMATION: peptide

<400> SEQUENCE: 13

Ser Arg Thr Glu Gly Asp Val
1               5

<210> SEQ ID NO 14
<211> LENGTH: 9
<212> TYPE: PRT
<213> ORGANISM: Artificial sequence
<220> FEATURE:
<223> OTHER INFORMATION: peptide

<400> SEQUENCE: 14

Cys Arg Gly Gly Lys Arg Ser Ser Cys
1               5

<210> SEQ ID NO 15
<211> LENGTH: 9
<212> TYPE: PRT
<213> ORGANISM: Artificial sequence
<220> FEATURE:
<223> OTHER INFORMATION: peptide

<400> SEQUENCE: 15

Cys Ser Leu Thr Gln Asp Gln Gly Cys 1               5

<210> SEQ ID NO 16
<211> LENGTH: 9
<212> TYPE: PRT
<213> ORGANISM: Artificial sequence
<220> FEATURE:
<223> OTHER INFORMATION: peptide

<400> SEQUENCE: 16

Cys Ala Asp Ala Gln Ala Asp Val Cys
1               5

<210> SEQ ID NO 17
<211> LENGTH: 9
<212> TYPE: PRT
<213> ORGANISM: Artificial sequence
<220> FEATURE:
<223> OTHER INFORMATION: peptide

<400> SEQUENCE: 17

Cys Arg Ala Lys Gly Arg Asp Ala Cys
1               5

<210> SEQ ID NO 18
<211> LENGTH: 9
<212> TYPE: PRT
<213> ORGANISM: Artificial sequence
<220> FEATURE:
<223> OTHER INFORMATION: peptide

<400> SEQUENCE: 18

Cys Lys Ala Ser Arg Leu Gly Arg Cys
1               5

<210> SEQ ID NO 19
<211> LENGTH: 9
<212> TYPE: PRT
<213> ORGANISM: Artificial sequence
<220> FEATURE:
<223> OTHER INFORMATION: peptide

<400> SEQUENCE: 19

Cys Arg Gly Ala Ser Met Asp Gly Cys
1               5

<210> SEQ ID NO 20
<211> LENGTH: 9
<212> TYPE: PRT
<213> ORGANISM: Artificial sequence
<220> FEATURE:
<223> OTHER INFORMATION: peptide

<400> SEQUENCE: 20

Cys Gly Arg Pro Gly Glu Ser Ser Cys
1               5

<210> SEQ ID NO 21
<211> LENGTH: 9
<212> TYPE: PRT
<213> ORGANISM: Artificial sequence
<220> FEATURE:
<223> OTHER INFORMATION: peptide

<400> SEQUENCE: 21

Cys Ser Arg Thr Glu Gly Asp Val Cys
1               5

```
<210> SEQ ID NO 22
<211> LENGTH: 9
<212> TYPE: PRT
<213> ORGANISM: Artificial sequence
<220> FEATURE:
<223> OTHER INFORMATION: peptide

<400> SEQUENCE: 22

Cys Ser Gly Arg Arg Gly Lys Ser Cys
1               5

<210> SEQ ID NO 23
<211> LENGTH: 8
<212> TYPE: PRT
<213> ORGANISM: Artificial sequence
<220> FEATURE:
<223> OTHER INFORMATION: peptide

<400> SEQUENCE: 23

Cys Arg Gly Gly Lys Arg Ser Ser
1               5

<210> SEQ ID NO 24
<211> LENGTH: 6
<212> TYPE: PRT
<213> ORGANISM: Artificial sequence
<220> FEATURE:
<223> OTHER INFORMATION: peptide

<400> SEQUENCE: 24

Arg Ala Lys Gly Arg Asp
1               5
```